US00PP16939P2

(12) United States Plant Patent
Laurens

(10) Patent No.: US PP16,939 P2
(45) Date of Patent: Aug. 1, 2006

(54) CRABAPPLE TREE NAMED 'X6114'

(50) Latin Name: ***Malus* sp.**
Varietal Denomination: X6114

(75) Inventor: Francois Laurens, Geaucouze (FR)

(73) Assignee: Agri-Obtentions SA, Guyancourt Cedex (FR)

( * ) Notice: Subject to any disclaimer, the term of this patent is extended or adjusted under 35 U.S.C. 154(b) by 0 days.

(21) Appl. No.: 11/031,329

(22) Filed: Jan. 6, 2005

Related U.S. Application Data

(60) Provisional application No. 60/536,173, filed on Jan. 12, 2004.

(51) Int. Cl.
*A01H 5/00* (2006.01)

(52) U.S. Cl. ..... Plt./173

(58) Field of Classification Search ..... Plt./173
See application file for complete search history.

*Primary Examiner*—Kent Bell
*Assistant Examiner*—June Hwu
(74) *Attorney, Agent, or Firm*—Stratton Ballew PLLC

(57) ABSTRACT

'X6114' is a new and distinct crabapple tree (*Malus* Mill.) notable for its late flowering and relatively low vigor.

3 Drawing Sheets

Latin name of the genus and species of the plant claimed: *Malus* sp.
Variety denomination: 'X6114'.

BACKGROUND OF THE INVENTION

'X6114' originated from a cross of 'Liberty' (seed parent, unpatented)×'White Angel' (pollen parent, unpatented), conducted as part of a controlled breeding program in Angers, France in 1985. 'X6114' has been asexually propagated by budding at Angers, France and Parker, Wash., USA, and has been shown to remain true to type over successive generations.

BRIEF SUMMARY OF THE INVENTION

'X6114' is a new and distinct apple tree notable for its late flowering and relatively low vigor as compared to 'Baugene' (unpatented), the variety most similar to 'X6114.' 'X6114' is clearly distinguishable from its parents by its fruit, which at 31 mm diameter is notably larger than 'White Angel' (12 mm to 20 mm) and smaller than 'Liberty' (70 mm to 80 mm).

BRIEF DESCRIPTION OF THE PHOTOGRAPHS

DETAILED BOTANICAL DESCRIPTION

Figure 1:
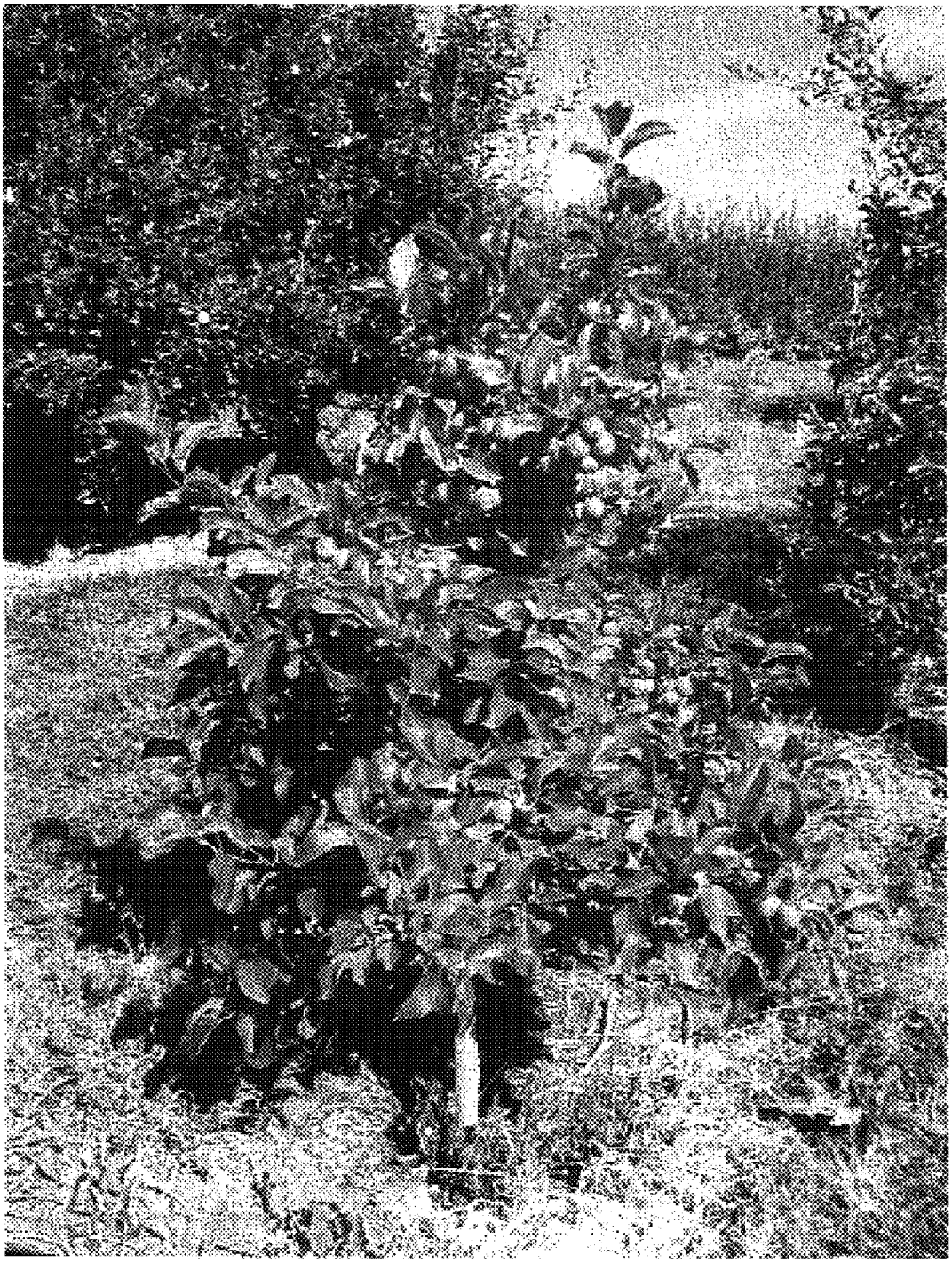
FIG. 1 shows the tree and leaves of the new cultivar.
Figure 2:
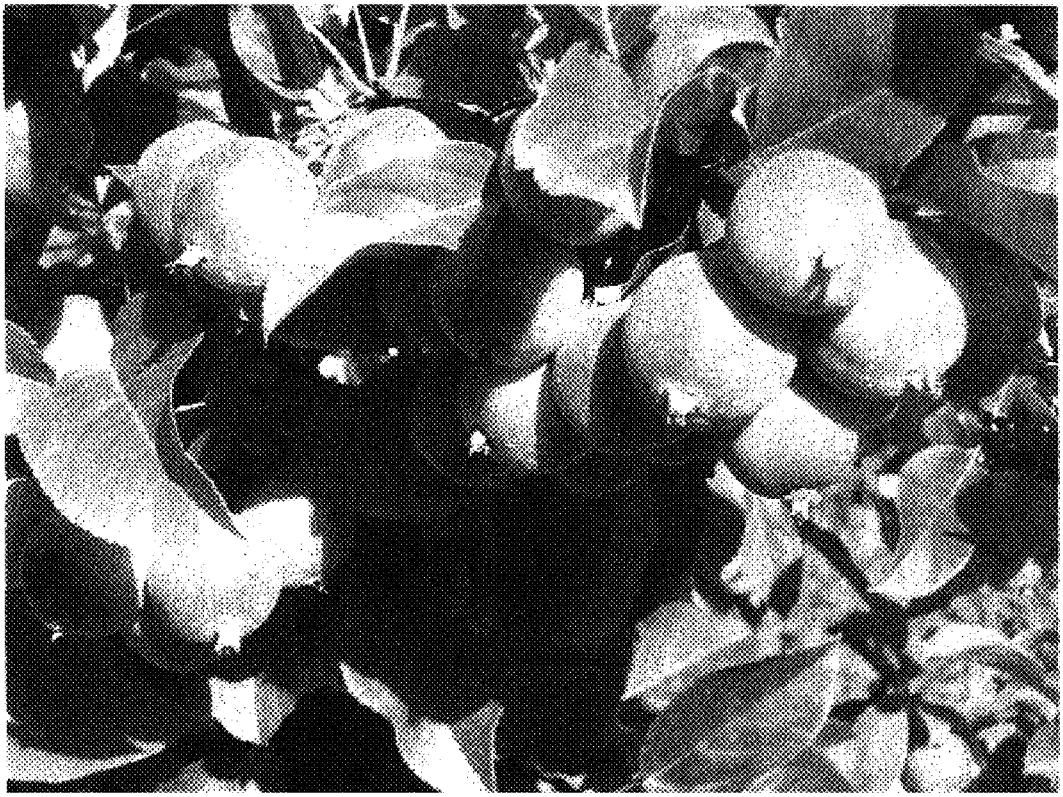
FIG. 2 shows the fruit and leaves of the new cultivar.
Figure 3:
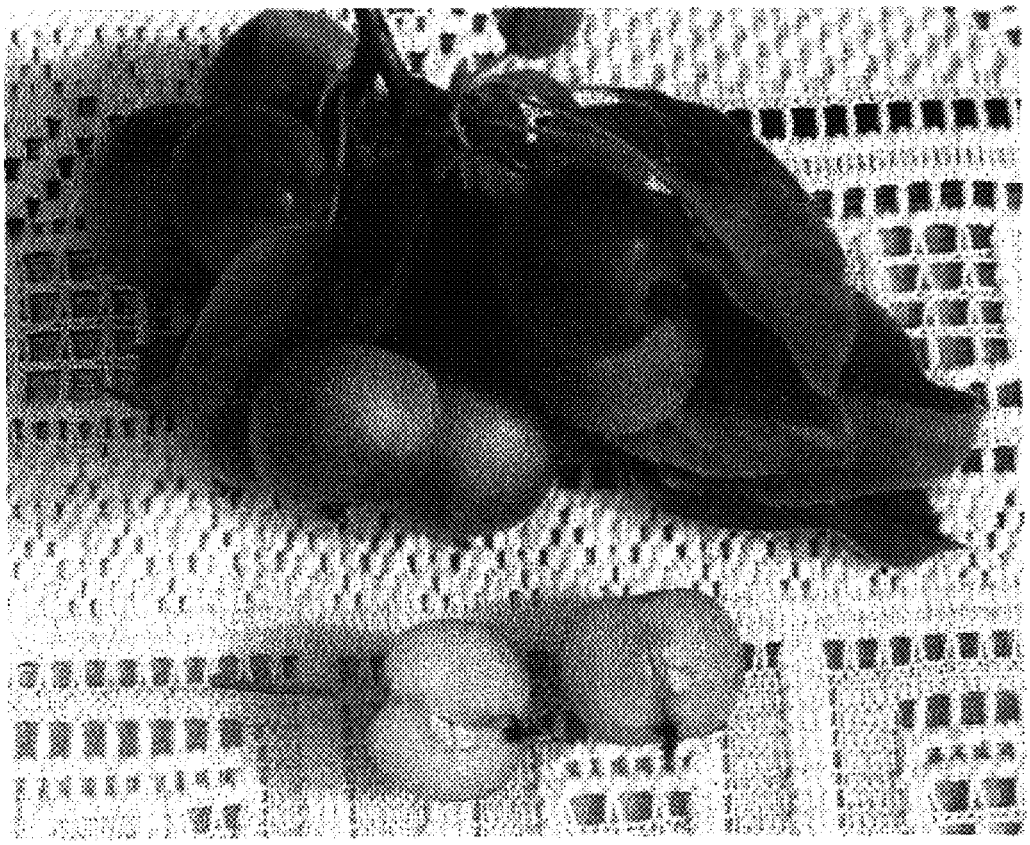
FIG. 3 shows whole and sectioned fruit, leaves, and seeds of the new cultivar.

The following is a detailed botanical description of the new and distinct apple tree, based on observations of three year old specimens grown at Parker, Wash., U.S.A. Color chart numbers refer to The Royal Horticultural Society Colour Chart. It should be understood that the botanical characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

1. Tree:
   - *Vigor.*—Moderate.
   - *Habit.*—Vase shaped.
   - *Size.*—Height, 1.8 m; diameter, 1.2 m.
   - *Trunk.*—Diameter 14 cm at graft union; bark texture smooth; lenticels prominent, elongated, length 0.5 to 0.9 cm, width 0.1 to 0.2 cm; trunk color brown N200D, new growth greyed-orange 176A; lenticels greyed-orange 165C.
   - *Branches* (*primary lateral*).—Length 31.2 cm; diameter 2.7 cm; smooth; branch color grey-brown 199C; lenticels elongated, length 0.3 to 0.4 cm, width 0.1 to 0.2 cm; greyed-yellow 161B.
   - *Winter hardiness.*—Hardy in area tested (Hardiness Zone 2).
2. Dormant one year old shoot:
   - *Color.*—Greyed-orange 176A.
   - *Internode length.*—2.4 to 4.0 cm.
   - *Number of lenticels.*—2 per $cm^2$.
3. Flower:
   - *Bud.*—Quantity per spur 3 to 6; elongated; smooth; hardy; length 0.5 to 0.6 cm; diameter 0.2 to 0.3 cm; green 143B, tip red-purple 67A.
   - *Flower size.*—Diameter 3.0 to 3.2 mm; Quantity per cluster 3 to 6.
   - *Petals.*—Quantity per flower 5; overlapping; length 2.2 to 2.3 cm; width 1.6 to 1.7 cm; apex obtuse; base oblique; upper and lower surface color white 155D with red-purple 70D venation when fully open.
   - *Sepals.*—Length 0.6 to 0.7 mm; width 0.2 to 0.3; green 143B.
   - *Pedicel.*—Length 3.5 cm; diameter 0.2 mm; green 143C.
   - *Pistil.*—Quantity 3, length 1.3 to 1.4 cm; smooth; yellow-green 150D.
   - *Stamen.*—Quantity per flower 20; length 0.9 to 1.3 cm; white 155D; pollen abundant, yellow 4A.

*Bloom period.*—Blooms annually; Late, March 28 to April 20 at Parker, Wash. (2004 growing season).

4. Leaf:
   *Attitude in relation to shoot.*—Upward.
   *Length.*—7.6 cm.
   *Width.*—5.0 cm.
   *Margin.*—Serrulate.
   *Shape.*—Ovate.
   *Color.*—Upper surface green137C; venation yellow-green 150D; lower surface green138B.
5. Petiole: Length 2.6 mm; diameter 0.2 mm; color greyed-orange 176A.
6. Fruit:
   *Size.*—Diameter 31 mm; height 31 mm.
   *General shape in profile.*—Truncate conical.
   *Ribbing.*—None.
   *Crowning at calyx end.*—None.
   *Depth of eye basin.*—0.0 to 0.1 mm.
   *Stalk.*—Diameter 2.0 mm; Length 25 mm; color green-yellow 1B, greyed-orange 163A.
   *Depth of stalk cavity.*—3.0 to 4.0 mm.
   *Width of stalk cavity.*—13.0 to 15.0 mm.
   *Skin texture.*—Smooth, moderate thickness.
   *Ground color of skin.*—Yellow-green 145A.
   *Over color of skin.*—Greyed-red 179A.
   *Amount of over color.*—40 to 60 percent of surface.
   *Pattern of over color.*—Blush.
   *Flesh.*—Texture coarse; moderate juiciness; astringent; greyed-yellow 160C.
   *Seeds.*—Length 5.0 mm, width 5.0 mm; ovateacuminate; white 155A.
   *Fruit drop.*—After multiple freezes.
7. Disease resistance: Somewhat resistant to scab, powdery mildew and blight (similar to parents).
   *Use.*—Pollenizer.

It is claimed:

1. We claim a new and distinct crabapple tree substantially as shown and described herein.

* * * * *

UNITED STATES PATENT AND TRADEMARK OFFICE

CERTIFICATE OF CORRECTION

PATENT NO. : PP 16,939 P2
APPLICATION NO. : 11/031329
DATED : August 1, 2006
INVENTOR(S) : Laurens It is certified that error appears in the above-identified patent and that said Letters Patent is hereby corrected as shown below:

Column 2,
Line 28, “mm” should read --cm--;
Line 34, “0.6 to 0.7 mm; width 0.2 to 0.3” should read --0.6 to 0.7 cm; width 0.2 to 0.3 cm--;
Line 36, “mm” should read --cm--; and Column 3,
Line 18, “mm” should read --cm--.

Signed and Sealed this

Twenty-first Day of November, 2006

JON W. DUDAS
*Director of the United States Patent and Trademark Office*